United States Patent
Rudek et al.

(10) Patent No.: US 10,464,954 B2
(45) Date of Patent: Nov. 5, 2019

(54) PROCESS FOR PREPARING 3-GLYCIDYLOXYPROPYLTRIALKOXYSILANES

(71) Applicant: Evonik Degussa GmbH, Essen (DE)

(72) Inventors: Markus Rudek, Buettelborn (DE); Susann Witzsche, Rheinfelden (DE); Stefan Bade, Michelbach le Haut (FR); Claudia Drescher, Loerrach (DE); Burkhard John, Rheinfelden (DE); Torsten Peterle, Rheinfelden (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 16/058,762

(22) Filed: Aug. 8, 2018

(65) Prior Publication Data

US 2019/0048031 A1    Feb. 14, 2019

(30) Foreign Application Priority Data

Aug. 9, 2017    (EP) .................................... 17185524

(51) Int. Cl.
    *C07F 7/18*    (2006.01)

(52) U.S. Cl.
    CPC .......... *C07F 7/1876* (2013.01); *C07F 7/1804* (2013.01)

(58) Field of Classification Search
    CPC .............................. C07F 7/1872; C07F 7/1804
    See application file for complete search history.

(56) References Cited

U.S. PATENT DOCUMENTS

| | | | |
|---|---|---|---|
| 3,825,567 A | 7/1974 | Kotzsch et al. | |
| 4,736,049 A | 4/1988 | Suzuki et al. | |
| 5,986,124 A | 11/1999 | Tachikawa et al. | |
| 6,402,961 B1 | 6/2002 | Bade et al. | |
| 8,039,646 B2 | 10/2011 | Bade et al. | |
| 2010/0036146 A1 | 2/2010 | Bade et al. | |

FOREIGN PATENT DOCUMENTS

| | | | |
|---|---|---|---|
| DE | 2 159 991 | 6/1973 | |
| EP | 0 277 023 | 8/1988 | |
| EP | 0 288 286 | 10/1988 | |
| EP | 0 548 974 | 6/1993 | |
| EP | 0 985 675 | 3/2000 | |
| EP | 1 694 687 | 8/2006 | |
| EP | 2 114 963 | 11/2009 | |
| JP | H01-28763 | 6/1989 | |
| SU | 415268 | 2/1974 | |
| WO | WO 200144255 | * 6/2001 | ................ C07F 7/18 |

OTHER PUBLICATIONS

S. Hauptmann, "Organische Chemie" [Organic Chemistry], 1st Edition, Germany, 1985, pp. 558 and 559 with English translation.

* cited by examiner

*Primary Examiner* — Noble E Jarrell
(74) *Attorney, Agent, or Firm* — Grüneberg and Myers PLLC

(57) ABSTRACT

A process can prepare a 3-glycidyloxypropylalkoxysilane of formula (I), $(R')O-(CH_2)_3-Si(OR)_3$ (I), where R groups are independently a methyl or ethyl group and R' represents an $H_2C(O)CHCH_2-$ group. The process includes reacting (i) a functionalized alkene of formula (II), $(R')O-C_3H_5$ (II), where R' represents an $H_2C(O)CHCH_2-$ group, with (ii) at least one hydroalkoxysilane of formula (III), $HSi(OR)_3$ (III), where R groups are independently a methyl or ethyl group. The reacting takes place in the presence of (iii) a Karstedt catalyst or a catalyst having hexachloroplatinic acid as a homogeneous catalyst, and (iv) 2-ethylhexanoic acid, isononanoic acid, or both. The process further includes obtaining a product of the reacting.

19 Claims, No Drawings

PROCESS FOR PREPARING 3-GLYCIDYLOXYPROPYLTRIALKOXYSILANES

BACKGROUND OF THE INVENTION

Field of the Invention

The invention relates to a process for preparing 3-glycidyloxypropyltrialkoxysilanes by hydrosilylation of allyl glycidyl ether in the presence of a Pt-based homogeneous catalyst and 2-ethylhexanoic acid and/or isononanoic acid as promoter.

Discussion of the Background

Glycidyl-functional silanes are important industrial intermediates or end products in organosilane chemistry. They find use as adhesion promoters in composite materials, for example in the paints and glass fibres industry, in foundry technology and in the adhesives industry; an important role is played by said compounds in the coating of optical glasses as well.

The preparation of 3-glycidyloxypropylalkoxysilanes is effected, for example, by reacting a trialkoxysilane that bears a hydrogen atom with allyl glycidyl ether in the presence of a hydrosilylation catalyst and can be described by the following general reaction equation:

$$CH_2(O)CHCH_2OCH_2CH=CH_2 + HSi(OR)_3 \rightarrow CH_2(O)CHCH_2OC_3H_6Si(OR)_3$$

with R=alkyl, e.g. methyl, ethyl, propyl. For instance, with R=methyl, the preparation of 3-glycidyloxypropyltrimethoxysilane is described and, with R=ethyl, the preparation of 3-glycidyloxypropyltriethoxysilane. By-products formed are isomers, $CH_2(O)CHCH_2OCH_2CH(Si(OR)_3)CH_3$ and a corresponding 8-membered heterocycle, and also glycidyloxytrialkoxysilane, propyltrialkoxysilane, propenyl glycidyl ether and tetraalkoxysilane, as well as high boiler components. Particularly the compounds that are difficult to remove by distillation, isomeric glycidyloxypropyltrialkoxysilane and the 8-membered heterocycle, require high separation intensities in a distillation column and long distillation times. The formation of corresponding propenyl glycidyl ethers and the formation of tetraalkoxysilane constitute high selectivity losses.

Hydrosilylation reactions of H-silanes with compounds containing a C═C double bond are conducted either batchwise or continuously; the hydrosilylation reaction is generally catalysed by precious metals. 3-Glycidyloxypropyltrialkoxysilanes are typically prepared under homogeneous catalysis with a Speier catalyst, $H_2PtCl_6$, or a Karstedt catalyst, divinyltetramethyldisiloxane-Pt (EP 0 277 023, EP 0 288 286, JP 128763 and DE 2 159 991 inter alia), or can alternatively be prepared under heterogeneous catalysis with precious metals (EP 0 548 974, U.S. Pat. No. 4,736,049).

If the hydrosilylation of allyl glycidyl ether with trimethoxysilane is conducted in the presence of a homogeneous Pt catalyst, it is observed that a non-negligible proportion of the allyl glycidyl ether used is isomerized and hence is no longer available for the hydrosilylation. This generally causes considerable losses of selectivity.

A further disadvantage of the homogeneous catalysts to date is the formation of colloidal Pt, which likewise leads to elevated by-product formation. Especially in the case of homogeneous catalysts of the Karstedt type, the formation of colloidal Pt is observed. As well as a reduction in the target product selectivity, there is isomerization of the olefin used, which, after isomerization, is no longer available for the hydrosilylation.

EP 1 694 687 discloses a process for preparing silicon compounds bearing fluoroalkyl groups by hydrosilylation of a fluoroolefin in the presence of a Pt catalyst, wherein one factor to be noted was the purity of the olefin used.

SU 415268 teaches preparing aminoalkylsilanes by hydrosilylation of allylamine, wherein this reaction is also conducted in the presence of a catalyst and with addition of an acid as promoter, one being acetic acid.

In addition, EP 0 985 675 discloses the use of an acid as promoter in the hydrosilylation of a hydrocarbon olefin for preparation of alkylsilanes. EP 0 985 675 mentions acetic acid as a preferred acid; cf. also U.S. Pat. No. 5,986,124.

It is common knowledge that an oxirane ring (cf. also the oxirane ring in epoxy and glycidyloxy functions) generally opens under the influence of an acid and thus constitutes a very reactive species. The oxirane ring is opened here either by acid catalysis or by any other nucleophile (S. Hauptmann, "Organische Chemie" [Organic Chemistry], 1st ed. 1985, VEB Verlag for Grundstoffindustrie, Leipzig, pages 558 ff.).

EP 2 114 963 shows that the preparation of glycidyloxyalkylalkoxysilanes can advantageously be conducted by hydrosilylation of olefin glycidyl ether in the presence of a Pt catalyst, a suitable solvent or diluent, and with addition of acetic acid under well-defined conditions with regard to selectivity and retention of the oxirane ring. On the industrial scale, however, it is found that acetic acid and corresponding acetoxy compounds—in some way or other—are also found at least in some proportion in the end product, which leads to higher acidities in the product, which in turn presents difficulties in one application of the product or another. In general, solvent-containing Karstedt catalysts, for example in xylene as a 2% solution, are supplied commercially.

The problem addressed by the present invention was that of providing an industrial process for preparing 3-glycidyloxypropylalkoxysilanes using a Pt-containing homogeneous catalyst, especially a Karstedt catalyst, which does not have the disadvantages set out above and where the selectivity and yield advantages are maintained at least in terms of order of magnitude. A particular aim was to provide a product free of acetic acid or comparable acidic volatile promoters, and also essentially free of organic solvent, especially hydrocarbons.

SUMMARY OF THE INVENTION

This and other objects have been achieved by the present invention, described at least in the following embodiments.

1. Process for preparing 3-glycidyloxypropylalkoxysilanes of the general formula (I)

$$(R')O-(CH_2)_3-Si(OR)_3 \quad (I)$$

in which R groups are independently a methyl or ethyl group and R' represents an $H_2C(O)CHCH_2-$ group, by reacting (i) a functionalized alkene of the general formula (II)

$$(R')O-C_3H_5 \quad (II)$$

in which R' represents an $H_2C(O)CHCH_2-$ group with (ii) at least one hydroalkoxysilane of the general formula (III)

$$HSi(OR)_3 \quad (III)$$

in which R groups are independently a methyl or ethyl group, preferably hydrotrimethoxysilane or hydrotriethoxysilane, in the presence of (iii) a Karstedt catalyst or a catalyst based on hexachloroplatinic acid as homogeneous catalyst and (iv) 2-ethylhexanoic acid and/or isononanoic acid and obtaining the product of the hydrosilylation.

2. Process according to Embodiment 1,
characterized in that
the olefin component (i) and the hydroalkoxysilane (ii) are used in a molar ratio of 0.8 to 1.3:1, preferably 1.03 to 1.25:1, more preferably 1.07 to 1.22:1, even more preferably 1.10 to 1.19:1, especially 1.12 to 1.17:1.0.

3. Process according to Embodiment 1 or 2,
characterized in that
the Karstedt catalyst (iii) as such (platinum(0) 1,3-divinyl-1,1,3,3-tetramethyldisiloxane complex; $O[Si(CH_3)_2 CH=CH_2]_2Pt$) or hexachloroplatinic acid ($H_2[PtCl_6]$, also called Speier catalyst) is used without the addition or use of any additional solvent.

4. Process according to any of Embodiments 1 to 3,
characterized in that
the catalyst (iii) on the basis of its Pt content is used in a molar ratio relative to the olefin component (i) of 1:2 000 000 to 1:50 000, preferably 1:1 000 000 to 1:100 000, more preferably 1:750 000 to 1:150 000, especially of 1:600 000 to 1:300 000.

5. Process according to any of Embodiments 1 to 4,
characterized in that
the Pt content of the catalyst (iii) and the 2-ethylhexanoic acid and/or isononanoic acid as promoter(s) (iv) are used in a molar ratio of 1:250 to 1:25 000, preferably 1:500 to 1:10 000, especially 1:1000 to 1:5000.

6. Process according to any of Embodiments 1 to 5,
characterized in that
in process variant A, components (i), (ii), (iii) and (iv) are premixed, fed to a reactor or reactor system for performance of the reaction and heated to a reaction temperature while mixing, or in process variant B, components (i), (iii) and (iv) are initially charged in or fed to a reactor or reactor system and heated to a reaction temperature while mixing, and component (ii) is metered in while mixing, or in process variant C, components (i) and (ii) are initially charged in or fed to a reactor or reactor system and heated to a reaction temperature while mixing, and components (iii) and (iv) are metered in as such or as a mixture while mixing, or in process variant D, components (ii), (iii) and (iv) are initially charged in or fed to a reactor or reactor system and heated to a reaction temperature while mixing, and component (i) is metered in while mixing.

7. Process according to any of Embodiments 1 to 6,
characterized in that
the reaction is conducted in a reactor at a reaction temperature between 80 and 230° C., preferably 100 to 200° C., and a pressure of 0.5 to 20 bar abs., preferably 0.5 to 4 bar abs., especially at ambient pressure.

8. Process according to any of Embodiments 1 to 7,
characterized in that
the reaction product is worked up by fractional distillation of the product mixture obtained after the reaction to obtain the target product.

9. Process according to any of Embodiments 1 to 8,
characterized in that
the reaction and workup are conducted batchwise or continuously.

10. Process according to any of Embodiments 1 to 9,
characterized in that
3-glycidyloxypropyltrimethoxysilane or 3-glycidyloxypropyltriethoxysilane is obtained in acetic acid- or acetoxy-free form.

11. Process according to any of Embodiments 1 to 10,
characterized in that
3-glycidyloxypropyltrimethoxysilane or 3-glycidyloxypropyltriethoxysilane is obtained, the product obtained having a pH of 3.5 to 5.5, preferably 4 to 5.

12. Process according to any of Embodiments 1 to 11,
characterized in that
3-glycidyloxypropyltrimethoxysilane or 3-glycidyloxypropyltriethoxysilane is obtained, the product obtained having a conductivity value of <10 µS/cm, preferably 0.0001 to <0.005 mS/cm, more preferably 0.001 to <0.004 mS/cm.

13. 3-Glycidyloxypropyltrimethoxysilane or 3-glycidyloxypropyltriethoxysilane obtained according to any of Embodiments 1 to 12.

DETAILED DESCRIPTION OF THE INVENTION

It has been found that, surprisingly, in an advantageous manner, by reacting (i) a functionalized alkene [also referred to hereinafter as olefin component for short] of the general formula (II)

$$(R')O—C_3H_5 \quad (II)$$

in which R' represents an $H_2C(O)CHCH_2$— group (called glycidyl group)

[also called allyl glycidyl ether or AGE for short]

with (ii) at least one hydroalkoxysilane of the general formula (III)

$$HSi(OR)_3 \quad (III)$$

in which R groups are independently a methyl or ethyl group, preferably hydrotrimethoxysilane [called TMOS for short] or hydrotriethoxysilane [called TEOS for short], in the presence of (iii) a Karstedt catalyst or a catalyst based on hexachloroplatinic acid as homogeneous catalyst and (iv) 2-ethylhexanoic acid (b.p. 226-229° C.) and/or isononanoic acid (b.p. 232-236° C.), in a simple and economically viable manner, a 3-glycidyloxypropylalkoxysilane of the general formula (I)

$$(R')O—(CH_2)_3—Si(OR)_3 \quad (I)$$

in which R groups are independently a methyl or ethyl group and R' represents a glycidyl group $H_2C(O)CHCH_2$— is advantageously obtained as the (target) product from the hydrosilylation of formula I with retention of the glycidyl function and in a form free of acetic acid or acetoxy groups and essentially free of organic solvent.

The present invention thus provides a process for preparing 3-glycidyloxypropylalkoxysilanes of the general formula (I)

$$(R')O—(CH_2)_3—Si(OR)_3 \quad (I)$$

in which R groups are independently a methyl or ethyl group and R' represents an $H_2C(O)CHCH_2$— group, by reacting
(i) a functionalized alkene [also referred to hereinafter as olefin component for short] of the general formula (II)

(R')O—C$_3$H$_5$  (II)

in which R' represents an H$_2$C(O)CHCH$_2$— group [also called allyl glycidyl ether or AGE for short]
with
(ii) at least one hydroalkoxysilane of the general formula (III)

HSi(OR)$_3$  (III)

in which R groups are independently a methyl or ethyl group, preferably hydrotrimethoxysilane [called TMOS for short] or hydrotriethoxysilane [called TEOS for short],
in the presence of
(iii) a Karstedt catalyst or a catalyst based on hexachloroplatinic acid as homogeneous catalyst and
(iv) 2-ethylhexanoic acid and/or isononanoic acid
and
obtaining the (target) product of the hydrosilylation.

In the process according to the invention, the olefin component (i) and the hydroalkoxysilane (ii) are used in a molar ratio of 0.8 to 1.3:1, preferably 1.03 to 1.25:1, more preferably 1.07 to 1.22:1, even more preferably 1.10 to 1.19:1, especially 1.12 to 1.17:1.0.

Moreover, in the process according to the invention, a Karstedt catalyst (iii) as such (platinum(0) 1,3-divinyl-1,1,3,3-tetramethyldisiloxane complex; O[Si(CH$_3$)$_2$CH=CH$_2$]$_2$ Pt) or hexachloroplatinic acid (H$_2$[PtCl$_6$], also called Speier catalyst) is used without the addition or use of any additional solvent.

Advantageously, in the process according to the invention, the Pt content (calculated as metallic platinum) in the reaction mixture is preferably adjusted to 1.2 to 3 ppm by weight, more preferably 1.5 to 2.5 ppm by weight, especially 1.7 to 2.3 ppm by weight, based on the overall reaction mixture, i.e. the sum total of the amounts of components (i), (ii), (iii) and (iv) used to perform the reaction.

The catalyst (iii) on the basis of its Pt content (calculated as metallic platinum) is advantageously used here in a molar ratio relative to the olefin component (i) of 1:2 000 000 to 1:50 000, preferably 1:1 000 000 to 1:100 000, more preferably 1:750 000 to 1:150 000, especially of 1:600 000 to 1:300 000.

In addition, in the process according to the invention, the Pt content (calculated as metallic platinum) of the catalyst (iii) and the 2-ethylhexanoic acid and/or isononanoic acid as promoter(s) (iv) are used in a molar ratio of 1:250 to 1:25 000, preferably 1:500 to 1:10 000, especially 1:1000 to 1:5000. It is particularly advantageous here that the aforementioned promoters 2-ethylhexanoic acid (b.p. 226-229° C.) and/or isononanoic acid (b.p. 232-236° C.) are in liquid form at room temperature and also under reaction conditions. Therefore, the 2-ethylhexanoic acid and/or the isononanoic acid, including a mixture of 2-ethylhexanoic acid and isononanoic acid, can be metered in a simple manner. Thus, the 2-ethylhexanoic acid or isononanoic acid or mixture thereof is also in dissolved form in the reaction mixture, meaning that there are advantageously no precipitates of promoters under reaction conditions, and so it is suitably possible to dispense with the use of a solvent Isononanoic acid in the present application is especially understood to mean a mixture of essentially branched C9 carboxylic acids, the preferred main constituent being 3,5,5-trimethylhexanoic acid, meaning that the isononanoic acid used in accordance with the invention has a "b.p."/boiling range of 232 to 236° C. (standard pressure). In addition, 2-ethylhexanoic acid is especially understood to mean a mixture of essentially branched C8 carboxylic acids, with 2-ethylhexanoic acid being the preferred main component, meaning that the 2-ethylhexanoic acid used in accordance with the invention has a "b.p."/boiling range of 226 to 229° C. (standard pressure). Furthermore, 2-ethylhexanoic acid and isononanoic acid are advantageously available on the market on the industrial scale and in industrial volumes. Explicitly excluded as promoters are thus carboxylic acids having a boiling point or boiling range below 220° C. (standard pressure), aromatic carboxylic acids, dicarboxylic acids and essentially pure unbranched carboxylic acids as such.

In the process according to the invention, the promoter in the form of 2-ethylhexanoic acid and/or isononanoic acid is preferably used at 0.05% to 2% by weight, more preferably 0.1% to 1.5% by weight, especially 0.2% to 1.2% by weight, based on the overall reaction mixture, i.e. the sum total of the amounts of components (i), (ii), (iii) and (iv) used to perform the reaction.

Suitably, the process according to the invention is performed in that
in process variant A, components (i), (ii), (iii) and (iv) are premixed, fed to a reactor or reactor system (for terminology see below) for performance of the reaction and heated to a reaction temperature while mixing, or
in process variant B, components (i), (iii) and (iv) are initially charged in or fed to a reactor or reactor system and heated to a reaction temperature while mixing, and component (ii) is metered in while mixing, or
in process variant C, components (i) and (ii) are initially charged in or fed to a reactor or reactor system and heated to a reaction temperature while mixing, and components (iii) and (iv) are metered in as such or as a mixture while mixing, or
in process variant D, components (ii), (iii) and (iv) are initially charged in or fed to a reactor or reactor system and heated to a reaction temperature while mixing, and component (i) is metered in while mixing.

Preferably, in the process according to the invention, the reaction is conducted in a reactor, preferably in a stirred tank, at a reaction temperature between 80 and 230° C., preferably 100 to 200° C., and a pressure of 0.5 to 20 bar abs., preferably 0.5 to 4 bar abs., especially at ambient pressure.

The process according to the invention is further conducted by working up the reaction product, i.e. the product mixture obtained on completion of reaction, wherein the product mixture obtained after the reaction (also called crude product for short) is fractionally distilled to obtain the target product, preferably in a distillation apparatus or unit under reduced pressure.

Thus, by the process according to the invention, 3-glycidyloxypropyltrimethoxysilane or 3-glycidyloxypropyltriethoxysilane is advantageously obtained, the product obtained having a pH of 3.5 to 5.5, preferably 4 to 5. In addition, a 3-glycidyloxypropyltrimethoxysilane or 3-glycidyloxypropyltriethoxysilane thus obtained advantageously has a conductivity value of ≤10 µS/cm, preferably 0.0001 to ≤0.005 mS/cm, more preferably 0.001 to ≤0.004 mS/cm.

For example, such 3-glycidyloxypropyltrimethoxy- or -triethoxysilanes obtained in accordance with the invention are also notable for an improvement in application properties in adhesives and sealants.

Therefore, the present invention also provides a 3-glycidyloxypropyltrimethoxysilane or 3-glycidyloxypropyltriethoxysilane which is obtained or obtainable by the process according to the invention and features a pH of 3.5 to 5.5, preferably 4 to 5, and a conductivity value of ≤10 µS/cm, preferably 0.0001 to ≤0.005 mS/cm, more preferably 0.001 to ≤0.004 mS/cm.

In general, the process according to the invention can be conducted as follows: Suitably, the plant used for performance of the present process is a stirred tank, a stirred tank cascade, a microstructured reactor (also called microreactor for short), a tubular reactor or flow reactor, a loop reactor or a combination or connected system of at least two of the aforementioned reactors (also referred to above and hereinafter as reactor or reactor system), which may be designed so as to be heatable or coolable, suitably has a stirring or swirling apparatus, at least one metering apparatus and optionally a reflux cooling system or a downstream distillation apparatus/unit, and can be operated under inert gas, for example nitrogen, and under reduced pressure or higher pressure than standard or ambient pressure. Suitably, the reaction apparatus and distillation apparatus is purged with dried nitrogen before use.

The process according to the invention can be performed by employing various process variants.

- For instance, components (i), (ii), (iii) and (iv) can be premixed, fed to the reactor or reactor system for performance of the reaction and, under active or non-forced mixing, referred to above and hereinafter as mixing for short, heated to a reaction temperature, for example with observation of the course of the reaction to a temperature in the range from 40 to 250° C., or
- components (i), (iii) and (iv) can be initially charged in or fed to the reactor or reactor system and heated up to a reaction temperature while mixing, and component (ii) can be metered into the existing component mixture while mixing, with adjustment (with or without closed-loop control), for example, to a temperature in the range from 40 to 250° C. while observing the reaction, or
- alternatively, components (i) and (ii) can be initially charged in the reactor or fed to the reactor or reactor system and heated up to a reaction temperature while mixing, for example to a temperature in the range from 40 to 250° C., and components (iii) and (iv) can be metered into the existing component mixture while mixing as such, i.e. individually or independently of one another, or as a mixture, with adjustment (with or without closed-loop control), for example, to a temperature in the range from 40 to 250° C. while observing the reaction or
- components (ii), (iii) and (iv) can be initially charged in or fed to a reactor or reactor system and heated up to a reaction temperature, for example to a temperature in the range from 40 to 250° C., while mixing, and component (i) can be metered into the existing component mixture while mixing, with adjustment (with or without closed-loop control), for example, to a temperature in the range from 40 to 250° C. while observing the reaction.

The conversion of the reaction mixture or of the reaction components correspondingly present in the reactor is preferably conducted at a temperature in the range from 100 to 220° C., and the product mixture thus obtained is suitably left to react while mixing for a further period of time, for example up to 2 hours—but not exclusively, suitably for 1 to 30 minutes, before the product mixture (crude product) is optionally transferred to a separate distillation unit and suitably worked up under gentle conditions, preferably under reduced pressure (vacuum), in a fractional distillation, to obtain the target product of the reaction, 3-glycidyloxypropyltrimethoxysilane (b.p. 248° C.) or 3-glycidyloxypropyltriethoxysilane [b.p. 120° C./2 mmHg], in high purity as the top product. In the process according to the invention, the reaction and workup can advantageously be conducted batchwise or continuously.

Thus, by the process according to the invention, 3-glycidyloxypropyltrimethoxysilane or 3-glycidyloxypropyltriethoxysilane can advantageously also be obtained on an industrial scale with excellent selectivity and with very high yield, i.e. in a particularly economically viable manner, and especially in acetic acid- and acetoxy-free form and in a form free of organic solvent.

The present invention is elucidated in detail by the examples which follow, without limiting the subject-matter of the invention.

EXAMPLES

Starting Materials/Abbreviations:
Karstedt catalyst: from Heraeus, Pt content 20.42% by weight
Acetic acid, from Sigma-Aldrich; purity≥99%
Propionic acid, from Merck; purity: ≥99%
Benzoic acid, from Carl Roth; content 99.5-100.5%
Heptanoic acid, from TCI; purity: >98%
2-Ethylhexanoic acid, from ABCR; purity: 99% (called 2-EHA for short)
3,5,5-Trimethylhexanoic acid (isononanoic acid), from TCI; purity: 99%
Decanoic acid, from Merck; purity≥98%
Dodecanoic acid, from Acros Organics; purity 98%
TMOS=trimethoxysilane, purity: 98%
AGE=allyl glycidyl ether, from Sigma-Aldrich, purity: ≥99%
DYN M=tetramethoxysilane
AGE=allyl glycidyl ether
cis-iso-AGE=cis-propenyl glycidyl ether
trans-iso-AGE=trans-propenyl glycidyl ether
iso-GLYMO=2-glycidyloxy-1-methylethyltrimethoxysilane
cyclo-GLYMO=1-dimethoxysila-2,5-dioxa-3-methoxymethylcyclooctane
GLYMO=3-glycidyloxypropyltrimethoxysilane
HB=high boilers
Analysis Methods:
Determination of Product Compositions by Means of Gas Chromatography:
Crude sample composition (sample from the crude product after reaction)
Instrument: 6850 Network GC System
Column: 19095J-123E HP5; 30 m/0.53 mm/2.65 μm
Temperature programme: 75° C.-3 min-10° C./min-275° C.-15 min
Pure sample composition (sample from the product after workup)
Instrument: 7820A GC System
Column: 19091J-413 HP5; 30 m/0.32 mm/0.25 μm
Temperature programme: 75° C.-3 min-10° C./min-275° C.-25 min
Conductivity Measurement:
Instrument: Metrohm 712 Conductometer
Method: SAA-1833; in μS/cm; toluene (from Merck, for analysis, ≥99%) is shaken with bidistilled water for 30 min. The aqueous phase is analysed. SAA-1834; in mS/cm; leave 2% sample (diluted in bidistilled water) to stand for 1 h, then analyse.
pH Determination:
Instrument: Metrohm 827 pH lab
Method: SAA-0268; 10 g sample plus 90 ml of bidistilled water, stir for 10 min, then analyse.

Comparative Example 1: (According to EP 2 114 963)

Allyl glycidyl ether was reacted continuously with trimethoxysilane to give 3-glycidyloxypropyltrimethoxysilane. The reaction was effected continuously in a tubular reactor by feeding in the raw materials (allyl glycidyl ether 9.6 kg/h and trimethoxysilane: 8 kg/h) together with the Pt Karstedt catalyst in the presence of acetic acid (0.05% by weight, based on the overall reaction mixture). The concentration of the catalyst based on metallic platinum was 2 ppm.

The Pt Karstedt catalyst was dissolved in 3-glycidyloxypropyltrimethoxysilane. The reaction temperature was about 160° C. The reaction was run with an excess of allyl glycidyl ether (molar ratio: allyl glycidyl ether:trimethoxysilane=1.28:1). The product mixture obtained after reaction was composed of:

| TMOS [%] | DYN M [%] | AGE [%] | cis-iso-AGE [%] | trans-iso-AGE [%] | iso-GLYMO [%] | cyclo-GLYMO [%] | GLYMO [%] | HB [%] |
|---|---|---|---|---|---|---|---|---|
| 0.2 | 0.4 | 0.4 | 6.4 | 3 | 0.3 | 0.1 | 87.3 | 1.9 |

The composition of the product mixture obtained after reaction was determined by means of gas chromatography.

The present product mixture was distilled to obtain the end product, and the acetic acid content after distillation was still around 200 ppm by weight.

When the process described above was conducted without the use of acetic acid as promoter, the following reaction product/crude product composition was obtained:

| TMOS [%] | DYN M [%] | AGE [%] | cis-iso-AGE [%] | trans-iso-AGE [%] | iso-GLYMO [%] | cyclo-GLYMO [%] | GLYMO [%] | HB [%] |
|---|---|---|---|---|---|---|---|---|
| 0.3 | 1.15 | 1.7 | 6.35 | 6.35 | 1.1 | 0.15 | 81 | 1.9 |

The advantages of the homogeneous Pt catalyst in the presence of acetic acid in combination with the use of the target product as solvent/diluent are the selectivity for the target product (GLYMO) and the reduction in the proportion of iso product and cyclo product, and suppression of the isomerization of the olefinic compound used. The reduction in by-product formation also led to easier distillability of the crude product and to an increase in quality, meaning that a lower separation intensity was required and shorter distillation times in the distillation batch when iso and cyclo product were present in smaller amounts.

Further Experimental Procedure:

The experiments which follow (comparative experiments 2 to 7 and inventive experiments 1 to 8) were conducted as follows:

AGE, TMOS, acid and Karstedt catalyst were initially charged in a stirred reactor. The reaction mixture was heated up to 100° C. (bottom temperature) while stirring within about 30 min. After the bottom temperature of 100° C. had been attained, the reaction mixture was kept at 100° C. for a further 90 min. Thereafter, the reaction mixture/product mixture was cooled down and then a sample was taken (called the crude sample).

The crude product obtained was then fractionally distilled under product-conserving conditions (reduced pressure) and the target product was obtained as the top product.

Comparative Example 2

Without added acid
without org. solvent
AGE/TMOS [mol/mol]=1.2/1
Pt conc.=2 ppm by weight (based on the overall reaction mixture)

The product mixture obtained after reaction had the following composition:

| TMOS [%] | DYN M [%] | AGE [%] | cis-iso-AGE [%] | trans-iso-AGE [%] | iso-GLYMO [%] | cyclo-GLYMO [%] | GLYMO [%] | HB [%] |
|---|---|---|---|---|---|---|---|---|
| 1.6 | 0.7 | 1.7 | 5.2 | 6.1 | 1.2 | 0.2 | 81.7 | 1.1 |

This crude product has only a yield of 81.7% based on the GLYMO target product and a comparatively marked proportion of 1.2% of iso-GLYMO, i.e. comparatively relatively low selectivity.

Comparative Example 3

With addition of acetic acid
without org. solvent
AGE/TMOS [mol/mol]=1.2/1
acetic acid, conc.=0.23% by weight (based on the overall reaction mixture)
Pt conc.=2 ppm by weight (based on the overall reaction mixture)

The product mixture obtained after reaction had the following composition:

| TMOS [%] | DYN M [%] | AGE [%] | cis-iso-AGE [%] | trans-iso-AGE [%] | iso-GLYMO [%] | cyclo-GLYMO [%] | GLYMO [%] | HB [%] |
|---|---|---|---|---|---|---|---|---|
| 0.7 | 0.8 | 0.4 | 7.5 | 3.4 | 0.3 | 0.02 | 85.2 | 0.9 |

This crude product has an undesirable proportion of acetic acid.

Comparative Example 4

With addition of propionic acid
without org. solvent
AGE/TMOS [mol/mol]=1.2/1
propionic acid, conc.=0.23% by weight (based on the overall reaction mixture)
Pt conc.=2 ppm by weight (based on the overall reaction mixture)

The product mixture obtained after reaction had the following composition:

| TMOS [%] | DYN M [%] | AGE [%] | cis-iso-AGE [%] | trans-iso-AGE [%] | iso-GLYMO [%] | cyclo-GLYMO [%] | GLYMO [%] | HB [%] |
|---|---|---|---|---|---|---|---|---|
| 0.05 | 0.6 | 0.3 | 7.6 | 3.5 | 0.3 | 0.03 | 85.9 | 0.9 |

Regrettably, this crude product had a proportion of acidic propionic acid, which, as is the case when acetic acid is used, had an adverse effect in some later product applications of the end product and hence was unsuitable for industrial practice.

Comparative Example 5

With addition of benzoic acid
with 0.8% by weight of MeOH as solvent, since usable only in dissolved form (based on the overall reaction mixture)
AGE/TMOS [mol/mol]=1.2/1
benzoic acid conc.=0.23% by weight (based on the overall reaction mixture)
Pt conc.=2 ppm by weight (based on the overall reaction mixture)

The product mixture obtained after reaction had the following composition:

| TMOS [%] | DYN M [%] | AGE [%] | cis-iso-AGE [%] | trans-iso-AGE [%] | iso-GLYMO [%] | cyclo-GLYMO [%] | GLYMO [%] | HB [%] |
|---|---|---|---|---|---|---|---|---|
| 0.2 | 0.8 | 0.5 | 6.9 | 4.0 | 0.5 | 0.1 | 84.2 | 1.6 |

When this aromatic carboxylic acid was used, there was a decline both in the selectivity (cf. iso-GLYMO) and in the yield of GLYMO.

Comparative Example 6

With addition of heptanoic acid
without org. solvent
AGE/TMOS [mol/mol]=1.2/1
heptanoic acid conc.=0.23% by weight (based on the overall reaction mixture)
Pt conc.=2 ppm by weight (based on the overall reaction mixture)

The product mixture obtained after reaction had the following composition:

| TMOS [%] | DYN M [%] | AGE [%] | cis-iso-AGE [%] | trans-iso-AGE [%] | iso-GLYMO [%] | cyclo-GLYMO [%] | GLYMO [%] | HB [%] |
|---|---|---|---|---|---|---|---|---|
| 0.2 | 0.6 | 0.3 | 7.1 | 3.9 | 0.5 | 0.1 | 85.7 | 1.2 |

It was found here that there was a decline in the selectivity; cf. iso-GLYMO.

Comparative Example 7

With addition of decanoic acid
with 0.8% by weight of MeOH as solvent (based on the overall reaction mixture)
AGE/TMOS [mol/mol]=1.2/1
decanoic acid conc.=0.23% by weight (based on the overall reaction mixture)
Pt conc.=2 ppm by weight (based on the overall reaction mixture)

Since decanoic acid was also solid at reaction temperature, it required the use of a solvent.

The product mixture obtained after reaction had the following composition:

| TMOS [%] | DYN M [%] | AGE [%] | cis-iso-AGE [%] | trans-iso-AGE [%] | iso-GLYMO [%] | cyclo-GLYMO [%] | GLYMO [%] | HB [%] |
|---|---|---|---|---|---|---|---|---|
| 0.2 | 0.8 | 0.7 | 6.5 | 4.3 | 0.6 | 0.1 | 84.3 | 1.5 |

It was found here too that the selectivity declines; cf. iso-GLYMO.

Comparative Example 8

With addition of dodecanoic acid
with 0.8% by weight of MeOH as solvent (based on the overall reaction mixture)
AGE/TMOS [mol/mol]=1.2/1
dodecanoic acid conc.=0.23% by weight (based on the overall reaction mixture)
Pt conc.=2 ppm by weight (based on the overall reaction mixture)

Dodecanoic acid was likewise solid at room temperature too; this entailed the use of a solvent here too.

The product mixture obtained after reaction had the following composition:

| TMOS [%] | DYN M [%] | AGE [%] | cis-iso-AGE [%] | trans-iso-AGE [%] | iso-GLYMO [%] | cyclo-GLYMO [%] | GLYMO [%] | HB [%] |
|---|---|---|---|---|---|---|---|---|
| 1.0 | 0.6 | 1.7 | 6.4 | 4.2 | 0.7 | 0.03 | 83.3 | 1.0 |

The result of the comparative experiment shows that selectivity and conversion here are declining; cf. iso-GLYMO and yield of GLYMO.

Example 1

With addition of 2-ethylhexanoic acid
without solvent
2-EHA conc.=0.23% by weight (based on the overall reaction mixture)
AGE/TMOS [mol/mol]=1.2/1
Pt conc.=2 ppm by weight (based on the overall reaction mixture)
The product mixture obtained after reaction had the following composition:

| TMOS [%] | DYN M [%] | AGE [%] | cis-iso-AGE [%] | trans-iso-AGE [%] | iso-GLYMO [%] | cyclo-GLYMO [%] | GLYMO [%] | HB [%] |
|---|---|---|---|---|---|---|---|---|
| 0.03 | 0.5 | 1.7 | 6.1 | 3.2 | 0.4 | 0.1 | 86.6 | 1.0 |

Example 2

With addition of 2-ethylhexanoic acid
without solvent
2-EHA conc.=1.2% by weight (based on the overall reaction mixture)
AGE/TMOS [mol/mol]=1.07/1
Pt conc.=2 ppm by weight (based on the overall reaction mixture)
The product mixture obtained after reaction had the following composition:

| TMOS [%] | DYN M [%] | AGE [%] | cis-iso-AGE [%] | trans-iso-AGE [%] | iso-GLYMO [%] | cyclo-GLYMO [%] | GLYMO [%] | HB [%] |
|---|---|---|---|---|---|---|---|---|
| 2.4 | 1.5 | 0.5 | 5.7 | 2.1 | 0.1 | 0.1 | 85.0 | 1.9 |

Example 3

With addition of 2-ethylhexanoic acid
without solvent
2-EHA conc.=0.24% by weight (based on the overall reaction mixture)
AGE/TMOS [mol/mol]=1.12/1
Pt conc.=2.2 ppm by weight (based on the overall reaction mixture)
The product mixture obtained after reaction had the following composition:

| TMOS [%] | DYN M [%] | AGE [%] | cis-iso-AGE [%] | trans-iso-AGE [%] | iso-GLYMO [%] | cyclo-GLYMO [%] | GLYMO [%] | HB [%] |
|---|---|---|---|---|---|---|---|---|
| 1.4 | 0.8 | 0.4 | 5.9 | 2.9 | 0.3 | 0.1 | 86.5 | 1.1 |

Example 4

With addition of 2-ethylhexanoic acid
without solvent
2-EHA conc.=1.2% by weight (based on the overall reaction mixture)
AGE/TMOS [mol/mol]=1.07/1
Pt conc.=2 ppm by weight (based on the overall reaction mixture)
The product mixture obtained after reaction had the following composition:

| TMOS [%] | DYN M [%] | AGE [%] | cis-iso-AGE [%] | trans-iso-AGE [%] | iso-GLYMO [%] | cyclo-GLYMO [%] | GLYMO [%] | HB [%] |
|---|---|---|---|---|---|---|---|---|
| 2.4 | 1.5 | 0.5 | 5.7 | 2.1 | 0.1 | 0.1 | 85.0 | 1.9 |

Example 5

With addition of 2-ethylhexanoic acid
without solvent
2-EHA conc.=0.22% by weight (based on the overall reaction mixture)
AGE/TMOS [mol/mol]=1.2/1
Pt conc.=4.3 ppm by weight (based on the overall reaction mixture)
The product mixture obtained after reaction had the following composition:

| TMOS [%] | DYN M [%] | AGE [%] | cis-iso-AGE [%] | trans-iso-AGE [%] | iso-GLYMO [%] | cyclo-GLYMO [%] | GLYMO [%] | HB [%] |
|---|---|---|---|---|---|---|---|---|
| 0.5 | 0.5 | 2.4 | 5.9 | 3.2 | 0.4 | 0.05 | 84.6 | 1.4 |

Example 6

With addition of 2-ethylhexanoic acid
without solvent
2-EHA conc.=0.47% by weight (based on the overall reaction mixture)
AGE/TMOS [mol/mol]=1.12/1
Pt conc.=2.2 ppm by weight (based on the overall reaction mixture)
The product mixture obtained after reaction had the following composition:

| TMOS [%] | DYN M [%] | AGE [%] | cis-iso-AGE [%] | trans-iso-AGE [%] | iso-GLYMO [%] | cyclo-GLYMO [%] | GLYMO [%] | HB [%] |
|---|---|---|---|---|---|---|---|---|
| 1.1 | 0.6 | 0.2 | 6.1 | 2.4 | 0.2 | 0.1 | 87.7 | 1.0 |

Example 7

With addition of 3,5,5-trimethylhexanoic acid (isononanoic acid)
without solvent
isononanoic acid conc.=0.60% by weight (based on the overall reaction mixture)
AGE/TMOS [mol/mol]=1.2/1
Pt conc.=2.1 ppm by weight (based on the overall reaction mixture)
The product mixture obtained after reaction had the following composition:

| TMOS [%] | DYN M [%] | AGE [%] | cis-iso-AGE [%] | trans-iso-AGE [%] | iso-GLYMO [%] | cyclo-GLYMO [%] | GLYMO [%] | HB [%] |
|---|---|---|---|---|---|---|---|---|
| 0.3 | 0.4 | 1.2 | 7.3 | 2.8 | 0.2 | 0.1 | 86.1 | 1.1 |

Example 8

With addition of 3,5,5-trimethylhexanoic acid (isononanoic acid)
without solvent
isononanoic acid conc.=0.48% by weight (based on the overall reaction mixture)
AGE/TMOS [mol/mol]=1.19/1
Pt conc.=2.3 ppm by weight (based on the overall reaction mixture)
The product mixture obtained after reaction had the following composition:

| TMOS [%] | DYN M [%] | AGE [%] | cis-iso-AGE [%] | trans-iso-AGE [%] | iso-GLYMO [%] | cyclo-GLYMO [%] | GLYMO [%] | HB [%] |
|---|---|---|---|---|---|---|---|---|
| 0.3 | 0.5 | 0.7 | 7.2 | 3.2 | 0.2 | 0.1 | 85.9 | 1.2 |

Summary of the Experimental Results:

According to the examples in which 2-ethylhexanoic acid and isononanoic acid were used as promoters for the reaction, excellent selectivities and at least comparable conversion rates, in some cases distinctly improved, were achieved. More particularly, products obtained in this way were advantageously free of disadvantageously acidic components, especially free of acetic acid and additionally include virtually no proportions of organic solvent, such as toluene, xylene or other hydrocarbons.

Any ranges mentioned herein include all values and subvalues between the lowest and highest limit of this range and the highest and lowest limits as well.

European patent application 17185524.0, filed Aug. 9, 2017, is incorporated herein by reference.

Numerous modifications and variations on the present invention are possible in light of the above teachings. It is therefore to be understood that, within the scope of the appended claims, the invention may be practiced otherwise than as specifically described herein.

The invention claimed is:

1. A process for preparing a 3-glycidyloxypropylalkoxysilane of formula (I)

(R')O—(CH$_2$)$_3$—Si(OR)$_3$  (I)

wherein R groups are independently a methyl or ethyl group and R' represents an H$_2$C(O)CHCH$_2$— group, the process comprising:
reacting by hydrosilylation
(i) a functionalized alkene of formula (II)

(R')O—C$_3$H$_5$  (II)

wherein R' represents an H$_2$C(O)CHCH$_2$— group
with
(ii) at least one hydroalkoxysilane of formula (III)

HSi(OR)$_3$  (III)

wherein R groups are independently a methyl or ethyl group, in the presence of
(iii) a Karstedt catalyst or a catalyst comprising hexachloroplatinic acid as a homogeneous catalyst, and
(iv) 2-ethylhexanoic acid, isononanoic acid, or both,
and
obtaining a product of the hydrosilylation.

2. The process according to claim 1, wherein the functionalized alkene (i) and the hydroalkoxysilane (ii) are used in a molar ratio of 0.8 to 1.3:1.

3. The process according to claim 1, wherein the Karstedt catalyst or catalyst comprising hexachloroplatinic acid is used without the addition or use of any additional solvent.

4. The process according to claim 1, wherein catalyst (iii), on a basis of a Pt content thereof, is used in a molar ratio relative to the functionalized alkene component (i) of 1:2,000,000 to 1:50,000.

5. The process according to claim 1, wherein a Pt content of catalyst (iii) and the 2-ethylhexanoic acid and/or isononanoic acid as promoter(s) (iv) are used in a molar ratio of 1:250 to 1:25,000.

6. The process according to claim 1, wherein
in process variant A, components (i), (ii), (iii) and (iv) are premixed, fed to a reactor or reactor system for performance of the reaction and heated to a reaction temperature while mixing, or
in process variant B, components (i), (iii) and (iv) are initially charged in or fed to a reactor or reactor system and heated to a reaction temperature while mixing, and component (ii) is metered in while mixing, or
in process variant C, components (i) and (ii) are initially charged in or fed to a reactor or reactor system and heated to a reaction temperature while mixing, and components (iii) and (iv) are metered in as such or as a mixture while mixing, or
in process variant D, components (ii), (iii) and (iv) are initially charged in or fed to a reactor or reactor system and heated to a reaction temperature while mixing, and component (i) is metered in while mixing.

7. The process according to claim 1, wherein the reacting is conducted in a reactor at a reaction temperature between 80 and 230° C. and at a pressure of 0.5 to 20 bar abs.

8. The process according to claim 1, further comprising: working up the product obtained from the reacting by fractional distillation of the product obtained from the reacting to obtain a target product.

9. The process according to claim 8, wherein the reacting and the working up are conducted batchwise or continuously.

10. The process according to claim 1, wherein the product obtained from the reacting comprises 3-glycidyloxypropyltrimethoxysilane or 3-glycidyloxypropyltriethoxysilane, which is in acetic acid- or acetoxy-free form.

11. The process according to claim 1, wherein the product obtained from the reacting comprises 3-glycidyloxypropyltrimethoxysilane or 3-glycidyloxypropyltriethoxysilane, and the product obtained from the reacting has a pH of 3.5 to 5.5.

12. The process according to claim 1, wherein the product obtained from the reacting comprises 3-glycidyloxypropyltrimethoxysilane or 3-glycidyloxypropyltriethoxysilane, and the product obtained from the reacting has a conductivity value of ≤10 µS/cm.

13. 3-Glycidyloxypropyltrimethoxysilane or 3-glycidyloxypropyltriethoxysilane obtained according to the process of claim 1.

14. The process according to claim 1, wherein the reacting is conducted in a reactor at a reaction temperature between 100 and 200° C. and at a pressure of 0.5 to 4 bar abs.

15. The process according to claim 1, wherein the product obtained from the reacting comprises 3-glycidyloxypropyltrimethoxysilane or 3-glycidyloxypropyltriethoxysilane, which is in acetic acid-free form.

16. The process according to claim 1, wherein the product obtained from the reacting comprises 3-glycidyloxypropyltrimethoxysilane or 3-glycidyloxypropyltriethoxysilane, which is in acetoxy-free form.

17. The process according to claim 1, wherein the reacting is carried out in the presence of 2-ethylhexanoic acid.

18. The process according to claim 1, wherein the reacting is carried out in the presence of isononanoic acid.

19. The process according to claim 1, wherein the reacting is carried out in the presence of 2-ethylhexanoic acid and isononanoic acid.

* * * * *